United States Patent [19]

Kawagishi et al.

[11] Patent Number: 4,882,266
[45] Date of Patent: Nov. 21, 1989

[54] SILVER HALIDE COLOR PHOTOGRAPHIC MATERIAL CONTAINING A PYRAZOLOAZOLE MAGENTA COUPLER

[75] Inventors: Toshio Kawagishi; Kiyoshi Nakazyo, both of Kanagawa, Japan

[73] Assignee: Fuji Photo Film Co., Ltd., Kanagawa, Japan

[21] Appl. No.: 307,020

[22] Filed: Feb. 7, 1989

Related U.S. Application Data

[63] Continuation of Ser. No. 224,245, Jul. 25, 1988, which is a continuation-in-part of Ser. No. 42,549, Apr. 27, 1987, abandoned, which is a continuation of Ser. No. 773,156, Sep. 6, 1985, abandoned.

[30] Foreign Application Priority Data

Sep. 6, 1984 [JP] Japan ............... 59-187203

[51] Int. Cl.$^4$ ............................... G03C 7/38
[52] U.S. Cl. ......................... 430/546; 430/387; 430/558
[58] Field of Search ............. 430/558 R, 387, 546

[56] References Cited

U.S. PATENT DOCUMENTS

| | | | |
|---|---|---|---|
| 3,725,067 | 4/1973 | Bailey | 430/558 |
| 4,562,146 | 12/1985 | Masuda et al. | 430/558 |
| 4,585,732 | 4/1986 | Kawagishi et al. | 430/558 |
| 4,590,153 | 5/1986 | Kawagishi et al. | 430/558 |
| 4,623,617 | 11/1986 | Kaneko et al. | 430/558 |
| 4,639,413 | 1/1987 | Kawagishi et al. | 430/558 |
| 4,639,415 | 1/1987 | Kaneko et al. | 430/558 |
| 4,665,015 | 5/1987 | Iijima et al. | 430/558 |

FOREIGN PATENT DOCUMENTS

| | | |
|---|---|---|
| 0178166 | 11/1984 | European Pat. Off. |
| 0178788 | 11/1984 | European Pat. Off. |
| 0178789 | 11/1984 | European Pat. Off. |
| 0182617 | 11/1984 | European Pat. Off. |
| 0183444 | 11/1984 | European Pat. Off. |
| 0183445 | 11/1984 | European Pat. Off. |
| 0137722 | 4/1985 | European Pat. Off. |
| 0200354 | 4/1985 | European Pat. Off. |
| 0145342 | 6/1985 | European Pat. Off. |
| 120147 | 11/1984 | Japan . |
| 120148 | 11/1984 | Japan . |
| 120150 | 11/1984 | Japan . |
| 120153 | 11/1984 | Japan . |
| 144647 | 12/1984 | Japan . |

*Primary Examiner*—Richard L. Schilling
*Attorney, Agent, or Firm*—Sughrue, Mion, Zinn, Macpeak & Seas

[57] ABSTRACT

A silver halide color photographic material comprising a support having coated thereon at least one silver halide emulsion layer, in which said silver halide emulsion layer or a layer adjacent thereto contains a pyrazoloazole magenta coupler having at least one substituted alkyl group represented by the formula (I):

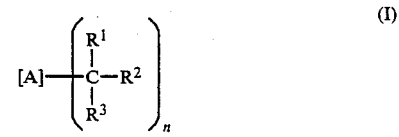

wherein [A] represents a pyrazoloazole magenta coupler residual group; $R^1$ is an alkyl group; $R^2$ and $R^3$ each is a hydrogen atom or a substituent, provided that both $R^2$ and $R^3$ are not hydrogen atoms at the same time; and n is 1, 2 or 3.

9 Claims, No Drawings

SILVER HALIDE COLOR PHOTOGRAPHIC MATERIAL CONTAINING A PYRAZOLOAZOLE MAGENTA COUPLER

This is a continuation of application Ser. No. 07/224,245, filed Jul. 25, 1988, which is a CIP of application Ser. No. 07/042,549 filed Apr. 27, 1987, now abandon which is a FWC of 06/773,156 filed Sept. 6, 1985, now abandoned.

FIELD OF THE INVENTION

The present invention relates to a silver halide color photographic material, and more particularly, to a silver halide color photographic material with improved light fastness of dye images.

BACKGROUND OF THE INVENTION

It is well known that, upon color development of a silver halide color photographic material, an oxidation product of an aromatic primary amine color developing agent reacts with a coupler to produce indophenol, indoaniline, indamine, azomethine, phenoxazine, phenazine or a like dye to thereby form a dye image. Among these couplers, those used for formation of magenta dye images include 5-pyrazolone, cyanoacetophenone, indazolone, pyrazolobenzimidazole and pyrazolotriazole couplers.

Magenta couplers which have hitherto been widely employed and undergone investigations are mostly 5-pyrazolone couplers. It is known that dye images formed by 5-pyrazolone couplers have superior fastness to heat and light but that the images contain a yellow component because of unnecessary absorption at about 430 nm, causing color turbidity.

In order to reduce the yellow component, there have conventionally been proposed coupler skeletons for formation of magenta dye images, such as a pyrazolobenzimidazole skeleton as described in British Pat. No. 1,047,612, an indazolone skeleton as described in U.S. Pat. No. 3,770,447 and a 1H-pyrazolo[5,1-c][1,2,4]triazole skeleton as described in U.S. Pat. No. 3,725,067. There have also recently been proposed a 1H-imidazo[1,2-b]pyrazole skeleton as described in European Patent 119,741, a 1H-pyrazolo[1,5-b][1,2,4]triazole skeleton as described in European Patent 119,860, a 1H-pyrazolo[1,5-d]tetrazole skeleton as described in *Research Disclosure* (hereinafter called "RD") 24220 (Jun., 1984) and a 1H-pyrazolo[1,5-b]pyrazole skeleton as described in RD 24230 (Jun.,1984).

Among these, a 1H-pyrazole[5,1-c][1,2,4]triazole coupler as described in U.S. Pat. No. 3,725,067 and British Pat. No. 1,252,418 and 1,334,515, a 1H-imidazo[1,2-b]pyrazole coupler as described in European Pat. No. 119,741, a 1H-pyrazolo[1,5-b][1,2,4]triazole coupler as described in European Pat. No. 119,860, a 1H-pyrazolo[1,5-d]tetrazole coupler as described in RD 24220 (Jun., 1984) and a 1H-pyrazole[1,5-b]pyrazole coupler as described in RD 24230 (Jun., 1984) form magenta dyes which show excellent absorption properties having no unnecessary absorption within the visible light range in a solvent such as ethyl acetate, dibutyl phthalate and the like.

However, among these couplers, azomethine dyes formed by a 1H-pyrazolo[5,1-c][1,2,4]triazole coupler had remarkably low fastness to light and markedly deteriorated the performances of color photographic light-sensitive materials, particularly color photographic light-sensitive materials for print. Azomethine dyes formed by other pyrazoloazole magenta couplers had light fastness insufficient for use in color photographic light-sensitive materials, particularly color photographic light-sensitive materials for print.

SUMMARY OF THE INVENTION

An object of the present invention is to provide a silver halide color photographic material having improved light fastness of dye images by employing a pyrazoloazole magenta coupler which produces an azomethine dye having excellent light fastness.

Another object of the present invention is to provide a silver halide color photographic material having improved light fastness of dye images and improved color reproducibility.

DETAILED DESCRIPTION OF THE INVENTION

The above identified objects of the present invention have been accomplished by using a silver halide color photographic material comprising a support having coated thereon at least one silver halide emulsion layer, in which said silver halide emulsion layer or a layer adjacent thereto contains a pyrazoloazole magenta coupler having substantial no dissolution in a developing solution and having at least one substituted alkyl group represented by the formula (I):

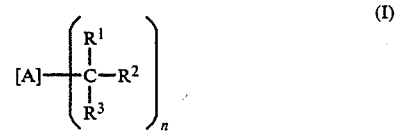

wherein [A] represents a pyrazoloazole magenta coupler residual group; $R^1$ is an alkyl group; $R^2$ and $R^3$ each is a hydrogen atom or a substituent, provided that both $R^2$ and $R^3$ are not hydrogen atoms at the same time; and n is 1, 2 or 3.

In other words, a pyrazolo-azole magenta coupler according to the present invention is characterized by that the pyrazolo-azole magenta coupler has substantial no dissolution in a developing solution and in addition, at least a

group is bonded directly to the pyrazolo-azole nucleus.

In contrast, a silver halide color photographic material containing a pyrazolo-azole magenta coupler which dissolves in a developing solution, when exposed to light and then developed, provides a color image having very low density and poor discrimination.

Specifically, the pyrazoloazole magenta coupler of the present invention is represented by formula (II):

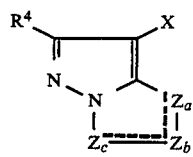 (II)

wherein X is a hydrogen atom or a group releasable upon coupling reaction; $R^4$ is a hydrogen atom, an alkyl group represented by

or other substituents; $Z_a$, $Z_b$ and $Z_c$ each is a methine group, a substituted methine group, a methylene group, a substituted methylene group, =N— or —NH—, provided that one of the $Z_a$—$Z_b$ bond and the $Z_b$—$Z_c$ bond is a double bond and the other is a single bond; when $Z_a$, $Z_b$ or $Z_c$ is a substituted methine group or a substituted methylene group, the substituent is an alkyl group represented by

or other substituents; at least one of $R^4$ and the substituents on the carbon atoms other than those at the coupling active sites is an alkyl group represented by

and the compound of the formula (II) may form a di- or polymer by X, $R^4$ or a substituent on the carbon atoms.

The term "di- or polymer" as used in the definition for the above described formula (II) means a compound containing at least two partial structures represented by the formula (II) in its molecule, and includes a bis compound and a polymer coupler. The term "polymer coupler" as herein used includes a homopolymer solely comprising a monomer having a moiety represented by the formula (II), and preferably having a vinyl group (the monomer having a vinyl group will hereinafter be referred to as a vinyl monomer), and a copolymer comprising said monomer and a non-color-forming ethylenically unsaturated monomer incapable of coupling with an oxidation product of an aromatic primary amine developing agent.

Among the pyrazoloazole magenta couplers of formula (II), those represented by formulae (III), (IV), (V), (VI) and (VII) are preferred:

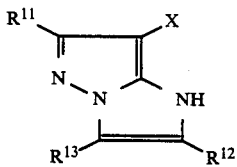 (III)

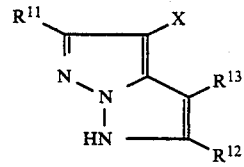 (IV)

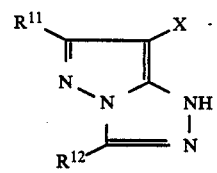 (V)

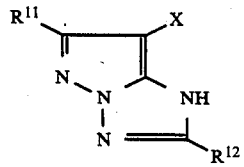 (VI)

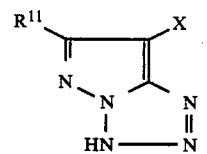 (VII)

In formulae (III) and (IV), at least one of the substituents represented by $R^{11}$, $R^{12}$ and $R^{13}$ is an alkyl group represented by

In formulae (V) and (VI), at least one of the substituents represented by $R^{11}$ and $R^{12}$ is an alkyl group represented by

In formula (VII), $R^{11}$ is an alkyl group represented by

The alkyl group represented by

will now be described in detail.

$R^1$ is a straight chain or branched chain or cyclic alkyl group (e.g., a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopentyl group, a cyclohexyl group, etc.). The alkyl group may contain one or more substituents. Examples of the substituent include a halogen atom (e.g., a fluorine atom, a chlorine atom, etc.), an alkenyl group (e.g., a vinyl group, etc.), an alkynyl group (e.g., a 1-propynyl group, etc.), a hydroxyl group, an amino group (e.g., ethylamino group, dimethylamino group, methyloctylamino group, etc.), a carboxyl group, an aryl group (e.g., a phenyl group, a 4-t-butylphenyl group, a 2,4-di-t-amylphenyl group, a 4-tetradecanamidophenyl group, etc.), a heterocyclic group (e.g., a 2-furyl group, a 2-thienyl group, a 2-pyrimidinyl group, a 2-benzothiazolyl group, etc.), a cyano group, an alkoxy group (e.g., a methoxy group, an ethoxy group, a 2-methoxyethoxy group, a 2-dodecyloxyethoxy group, a 2-methanesulfonylethoxy group, etc.), an aryloxy group (e.g., a phenoxy group, a 2-methylphenoxy group, a 4-t-butylphenoxy group, etc.), a heterocyclic oxy group (e.g., a 2-benzimidazolyloxy group, etc.), an acyloxy group (e.g., an acetoxy group, a hexadecanoyloxy group, etc.), a carbamoyloxy group (e.g., an N-phenylcarbamoyloxy group, an N-ethylcarbamoyloxy group, etc.), a silyloxy group (e.g., a trimethylsilyloxy group, etc.), a sulfonyloxy group (e.g., a dodecylsulfonyloxy group, etc.), an acylamino group (e.g., an acetamido group, a benzamido group, a tetradecanamido group, an α-(2,4-di-t-amylphenoxy)butyramido group, a γ-(3-t-butyl-4-hydroxyphenoxy)butyramido group, an α-[4-(4-hydroxyphenylsulfonyl)phenoxy]decanamido group, etc.), an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-[α-(3-t-butyl-4-hydroxyphenoxy)-dodecanamido]anilino group, etc.), a ureido group (e.g., a phenylureido group, a methylureido group, an N,N-dibutylureido group, etc.), an imido group (e.g., an N-succinimido group, a 3-benzylhydantoinyl group, a 4-(2-ethylhexanoylamino)phthalimido group, etc.), a sulfamoylamino group (e.g., an N,N-dipropylsulfamoylamino group, an N-methyl-N-decylsulfamoylamino group, etc.), an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.), an arylthio group (e.g., a phenylthio group, a 2-butoxy-5-t-octylphenylthio group, a 3-pentadecylphenylthio group, a 2-carboxyphenylthio group, a 4-tetradecanamidophenylthio group, etc.), a heterocyclic thio group (e.g., a 2-benzothiazolylthio group, etc.), an alkoxycarbonylamino group (e.g., a methoxycarbonylamino group, a tetradecyloxycarbonylamino group, etc.), an aryloxycarbonylamino group (e.g., a phenylcarbonylamino group, a 2,4-di-tert-butylphenoxycarbonylamino group, etc.), a sulfonamido group (e.g., a methanesulfonamido group, a hexadecanesulfonamido group, a benzenesulfonamido group, a p-toluenesulfonamido group, an octadecanesulfonamido group, a 2-methoxy-5-t-butylbenzenesulfonamido group, etc.), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N-[3-(2,4-di-tert-amylphenoxy)propyl]carbamoyl group, etc.), an acyl group (e.g., an acetyl group, a (2,4-di-tert-amylphenoxy)acetyl group, a benzoyl group, etc.), a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group), a sulfonyl group (e.g., a methanesulfonyl group, an octanesulfonyl group, a benzenesulfonyl group, a toluenesulfonyl group, etc.), a sulfinyl group (e.g., an octanesulfinyl group, a dodecylsulfinyl group, a phenylsulfinyl group, etc.), an alkoxycarbonyl group (e.g., a methoxycarbonyl group, a butyloxycarbonyl group, a dodecyloxycarbonyl group, an octadecyloxycarbonyl group, etc.), and an aryloxycarbonyl group (e.g., a phenyloxycarbonyl group, a 3-pentadecylphenyloxycarbonyl group, etc.).

$R^2$ and $R^3$ each is a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, a hydroxyl group, an amino group or a carboxyl group. More specifically, $R^2$ and $R^3$ each is a hydrogen atom, a halogen atom (e.g., a fluorine atom, a chlorine atom, etc.), an alkyl group (e.g., a methyl group, an ethyl group, a propyl group, a 2,2-dimethylpropyl group, an n-butyl group, a t-butyl group, a trifluoromethyl group, a tridecyl group, a 3-(2,4-di-t-amylphenoxy)propyl group, an allyl group, a 2-dodecyloxyethyl group, a 3-phenoxypropyl group, a 2-hexylsulfonylethyl group, a cyclopentyl group, a benzyl group, etc.), an aryl group (e.g., a phenyl group, a 4-t-butylphenyl group, a 2,4-di-t-amylphenyl group, a 4-tetradecanamidophenyl group, etc.), a heterocyclic group (e.g., a 2-furyl group, a 2-thienyl group, a 2-pyrimidinyl group, a 2-benzothiazolyl group, etc.), a cyano group, an alkoxy group (e.g., a methoxy group, an ethoxy group, a 2-methoxyethoxy group, a 2-dodecyloxyethoxy group, a 2-methanesulfonylethoxy group, etc.), an aryloxy group (e.g., a phenoxy group, a 2-methylphenoxy group, a 4-t-butylphenoxy group, etc.), a heterocyclic oxy group (e.g., a 2-benzimidazolyloxy group, etc.), an acyloxy group (e.g., an acetoxy group, a hexadecanoyloxy group, etc.), a carbamoyloxy group (e.g., an N-phenylcarbamoyloxy group, an N-ethylcarbamoyloxy group, etc.), a silyloxy group (e.g., a trimethylsilyloxy group, etc.), a sulfonyloxy group (e.g., a dodecylsulfonyloxy group, etc.), an acylamino group (e.g., an acetamido group, a benzamido group, a tetradecanamido group, an α-(2,4-di-t-amylphenoxy)butyramido group, a γ-(3-t-butyl-4-hydroxyphenoxy)butyramido group, an α-[4-(4-hydroxyphenylsulfonyl)phenoxy]decanamido group, etc.), an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-[α-(3-t-butyl-4-hydroxyphenoxy)-dodecanamido]anilino group, etc.), a ureido group (e.g., a phenylureido group, a methylureido group, an N,N- dibutylureido group, etc.), an imido group (e.g., an N-succinimido group, a 3-benzylhydantoinyl group, a 4-(2-ethylhexanoylamino)phthalimido group, etc.), a sulfamoylamino group (e.g., an N,N-dipropylsulfamoylamino group, an N-methyl-N-decylsulfamoylamino group, etc.), an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.), an arylthio group (e.g., a phenylthio group, a 2-butoxy-5-t-octylphenylthio group, a 3-pentadecylphenylthio group, a 2-carboxyphenylthio group, a 4-tetradecanamidophenylthio group, etc.), a heterocyclic thio group (e.g., a 2-benzothiazolylthio group, etc.), an alkoxycarbonylamino group (e.g., a methoxycarbonylamino group, a tetradecyloxycarbonylamino group, etc.), an aryloxycarbonylamino group (e.g., a phenylcarbonylamino group, a 2,4-di-tert-butylphenoxy carbonylamino group, etc.), a sulfonamido group (e.g., a methanesulfonamido group, a hexadecanesulfonamido group, a benzenesulfonamido group, a p-toluenesulfonamido group, an octadecanesulfonamido group, a 2-methoxy-5-t-butylbenzenesulfonamido group, etc.), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N-[3-(2,4-di-tert-amylphenoxy)propyl]carbamoyl group, etc.), an acyl group (e.g., an acetyl group, a (2,4-di-tert-amylphenoxy)acetyl group, a benzoyl group, etc.), a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group), a sulfonyl group (e.g., a methanesulfonyl group, an octanesulfonyl group, a benzenesulfonyl group, a toluenesulfonyl group, etc.), a sulfinyl group (e.g., an octanesulfinyl group, a dodecylsulfinyl group, a phenylsulfinyl group, etc.), an alkoxycarbonyl group (e.g., a methoxycarbonyl group, a butyloxycarbonyl group, a dodecyloxycarbonyl group, an octadecyloxycarbonyl group, etc.), an aryloxycarbonyl group (e.g., a phenyloxycarbonyl group, a 3-pentadecylphenyloxycarbonyl group, etc.), a hydroxyl group, an amino group (e.g., an ethylamino group, a dimethylamino group, a methyloctylamino group, etc.), or a carboxyl group.

In formulae (III) and (IV), among the substituents represented by $R^{11}$, $R^{12}$ and $R^{13}$, the substituent other than the alkyl group represented by

is preferably the groups aforementioned for $R^2$ and $R^3$.

In formulae (V) and (VI), among the substituents represented by $R^{11}$ and $R^{12}$, the substituent other than the alkyl group represented by

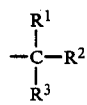

is preferably the groups aforementioned for $R^2$ and $R^3$.

In formulae (III), (IV), (V), (VI) and (VII), X is a hydrogen atom, a halogen atom (e.g., a chlorine atom, a bromine atom, an iodine atom, etc.), a carboxy group, a group bonded via an oxygen atom (e.g., an acetoxy group, a propanoyloxy group, a benzoyloxy group, a 2,4-dichlorobenzoyloxy group, an ethoxyoxazoyloxy group, a pyruvinyloxy group, a cinnamoyloxy group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.), a group bonded via a nitrogen atom (e.g., a benzenesulfonamido group, an N-ethyltoluenesulfonamido group, a heptafluorobutanamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl-2,4-dioxo-3-oxazolidinyl group, a 1-benzylethoxy-3-hydantoinyl group, a 2N-1,1-dioxo-3(2H)oxo-1,2-benzisothiazoyly group, a 2-oxo-1,2-dihydro-1-pyridinyl group, an imidazolyl group, a pyrazolyl group, a 3,5-diethyl-1,2,4-triazol-1-yl group, a 5- or 6-bromobenzotriazol-1-yl group, a 5-methyl-1,2,3,4-triazol-1-yl group, a benzimidazolyl group, a 3-benzyl-1-hydantoinyl group, a 1-benzyl-5-hexadecyloxy-3-hydantoinyl group, a 5-methyl-1-tetrazolyl group, etc.), an arylazo group (e.g., a 4-methoxyphenylazo group, a 4-pivaloylaminophenylazo group, a 2-naphthylazo group, a 3-methyl-4-hydroxyphenylazo group, etc.), or a group bonded via a sulfur atom (e.g., a phenylthio group, a 2-carboxyphenylthio group, a 2-methoxy-5-t-octylphenylthio group, a 4-methanesulfonylphenylthio group, a 4-octanesulfonamidophenylthio group, a 2-butoxyphenylthio group, a 2-(2-hexanesulfonylethyl)-5-t-octylphenylthio group, a benzylthio group, a 2-cyanoethylthio group, a 1-ethoxycarbonyltridecylthio group, a 5-phenyl-2,3,4,5-tetrazolylthio group, a 2-benzothiazolylthio group, 2-dodecylthio-5-thiophenylthio group, a 2-phenyl-3-dodecyl-1,2,4-triazolyl-5-thio group, etc.).

It is most preferred in formulae (V) and (VI) that X be a group other than a hydrogen atom or a carboxy group, i.e., is selected from the groups for X earlier recited other than a hydrogen atom or a carboxy group.

In the coupler of formula (III), $R^{12}$ and $R^{13}$ may be taken together to form a non-aromatic 5- to 7-membered ring.

In the coupler of formula (IV), $R^{12}$ and $R^{13}$ may be taken together to form a 5- to 7-membered saturated, unsaturated or aromatic ring.

When $R^{11}$, $R^{12}$, $R^{13}$ or X is a divalent group to form a bis compound, $R^{11}$, $R^{12}$ and $R^{13}$ each is preferably a substituted or unsubstituted alkylene group (e.g., a methylene group, an ethylene group, a 1,10 decylene group, —CH$_2$CH$_2$—O—CH$_2$—, etc.), a substituted or unsubstituted phenylene group (e.g., a 1,4-phenylene group, a 1,3-phenylene group

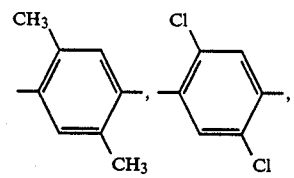

etc.), —NHCO—R$^{14}$—CONH—group wherein R$^{14}$ is a substituted or unsubstituted alkylene group or a phenylene group (e.g., —NHCOCH$_2$CH$_2$CONH—,

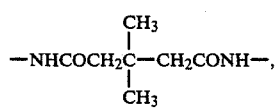

etc.) or an —S—R$^{15}$—S—group wherein R$^{15}$ is a substituted or unsubstituted alkylene group (e.g., —S—CH$_2$CH$_2$—S—,

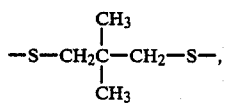

etc.) and X is a divalent group formed from the aforementioned monovalent group at an appropriate position.

When the moieties represented by formulae (III), (IV), (V), (VI) and (VII) are contained in ethylenically unsaturated monomers, the linking groups represented by R$^{11}$, R$^{12}$, R$^{13}$ and X include an alkylene group (a substituted or unsubstituted alkylene group, such as a methylene group, an ethylene group, a 1,10-decylene group and —CH$_2$CH$_2$OCH$_2$CH$_2$—), a phenylene group (a substituted or unsubstituted phenylene group, such as a 1,4-phenylene group, a 1,3-phenylene group,

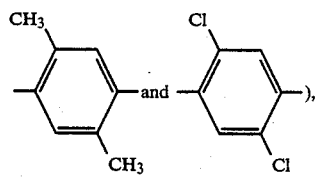

—NHCO—, —CONH—, —O—, —OCO—, an aralkylene group (e.g.,

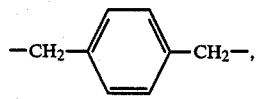

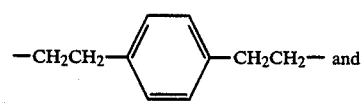

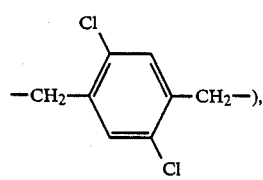

and combinations thereof. Preferable linking groups include the following: —NHCO—, —CH$_2$CH$_2$—,

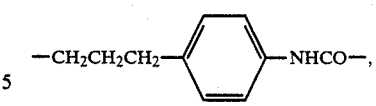

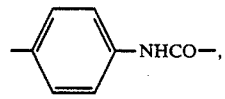

—CH$_2$CH$_2$NHCO—,

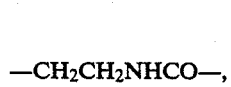

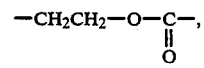

—CONH—CH$_2$CH$_2$NHCO—, —CH$_2$CH$_2$O—CH$_2$CH$_2$—NHCO—and

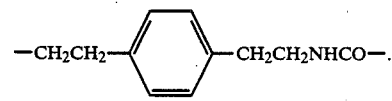

The ethylenically unsaturated group contained in the vinyl monomer may have substituents other than those mentioned in formula (III), (IV), (V), (VI) or (VII). Preferred substituents include a hydrogen atom, a chlorine atom or a lower alkyl group having 1 to 4 carbon atoms (e.g., a methyl group, an ethyl group, etc.).

Monomers containing moieties represented by formula (III), (IV), (V), (VI) or (VII) may form a copolymer with a non-color-forming ethylenically unsaturated monomer incapable of coupling with an oxidation product of an aromatic primary amine developing agent.

The non-color-forming ethylenically unsaturated monomer incapable of coupling with an oxidation product of an aromatic primary amine developing agent includes acrylic acids, such as acrylic acid, α-chloroacrylic acid and an α-alacrylic acid (e.g., methacrylic acid), esters or amides of these acrylic acids (e.g., acrylamide, n-butylacrylamide, t-butylacrylamide, diacetoneacrylamide, methacrylamide, methyl acrylate, ethyl acrylate, n-propyl acrylate, n-butyl acrylate, t-butyl acrylate, isobutyl acrylate, 2-ethylhexyl acrylate, n-octyl acrylate, lauryl acrylate, methyl methacrylate, ethyl methacrylate, n-butyl methacrylate, β-hydroxy methacrylate, etc.), methylenebisacrylamide, vinyl esters (e.g., vinyl acetate, vinyl propionate, vinyl laurate, etc.), acrylonitrile, methacrylonitrile, aromatic vinyl compounds (e.g., styrene and its derivatives, vinyltoluene, divinylbenzene, vinylacetophenone, sulfostyrene, etc.), itaconic acid, citraconic acid, crotonic acid, vinylidene chloride, vinyl alkyl ethers (e.g., vinylethyl ether, etc.), maleic acid, maleic anhydride, maleic esters, N-vinyl-2-pyrrolidone, N-vinylpyridine, 2-, 3- or 4-vinylpyridine, and the like.

These non-color-forming ethylenically unsaturated monomers can be used alone or in combination. For example, combinations of n-butylacrylate and methyl acrylate, styrene and methacrylic acid, methacrylic acid and acrylamide, and methyl acrylate and diacetone acrylamide and the like can be used.

As is known in the field of polymer color couplers, non-color-forming ethylenically unsaturated monomers to be subjected to copolymerization with solid water-insoluble monomeric couplers may be selected such that the physical properties and/or chemical properties of the formed copolymers such as solubility, compatibility with the binder of the photographic colloid composition such as gelatin, flexibility, heat stability and the like are advantageously influenced.

The polymer coupler used in accordance with the present invention may be or may not be water-soluble, but a polymer coupler latex is particularly preferred.

Among couplers represented by formulae (III), (IV), (V), (VI) and (VII), particularly preferred are those represented by formulae (III), (IV), (VI) and (VII), and mot particularly preferred are those represented by formula (VI) in terms of the hues of the color-forming dyes and shelf stability.

Specific examples of the couplers of formulae (III), (IV), (V), (VI) and (VII) and processes for synthesizing them are described in the following literature:

The couplers of formula (III) are described in U.S. Pat. No. 4,500,630 and European Pat. No. 119,741A; the couplers of formula (IV) in Japanese Patent Application (OPI) No. 43659/85 (the term "OPI" as used herein refers to a "published unexamined Japanese patent application"); the couplers of formula (V) in U.S. Pat. Nos. 3,705,896 and 3,725,067 and the like; the couplers of formula (VI) in European Patent 119,860A (corresponding to U.S. patent applicaiton Ser. No. 590,818, filed on Mar. 19, 1984) and the like; and the couplers of formula (VII) in Japanese Patent Application (OPI) No. 33552/85.

Specific examples of the representative magenta couplers of the present invention and ethylenically unsaturated monomers thereof will be shown below, but these examples do not limit the scope of the present invention in any manner:

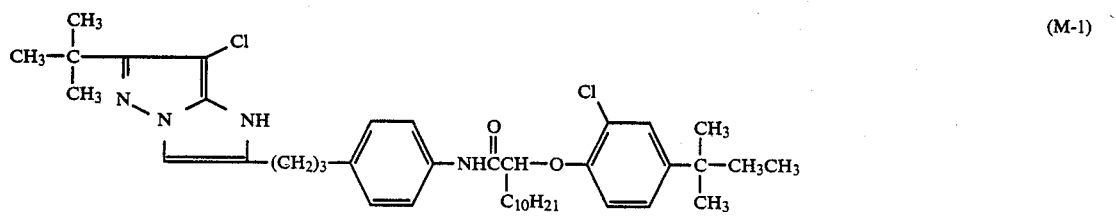
(M-1)

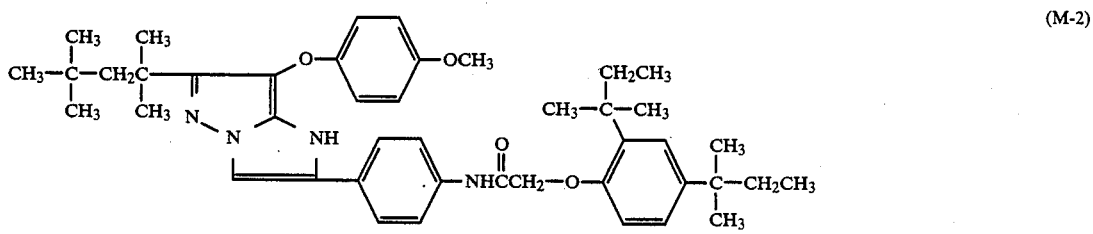
(M-2)

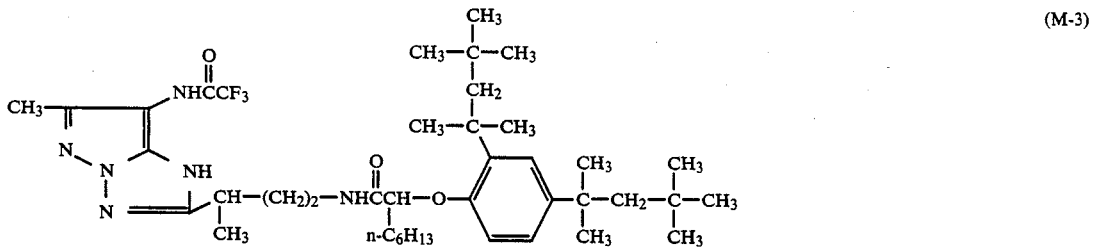
(M-3)

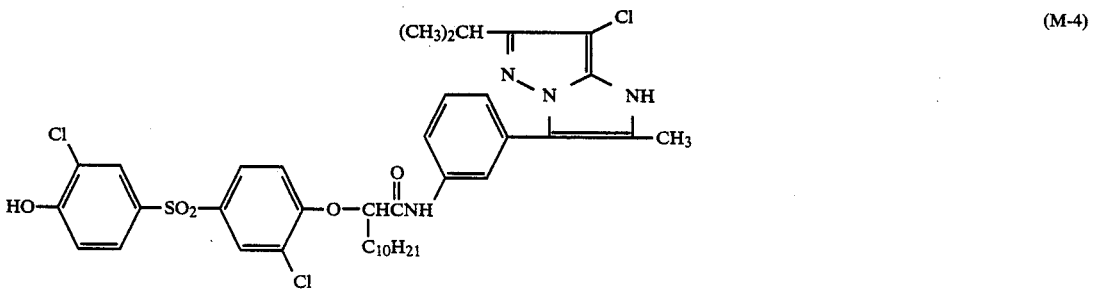
(M-4)

(M-5)

-continued
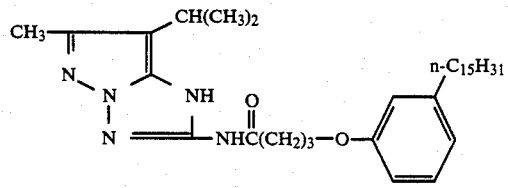 (M-6)
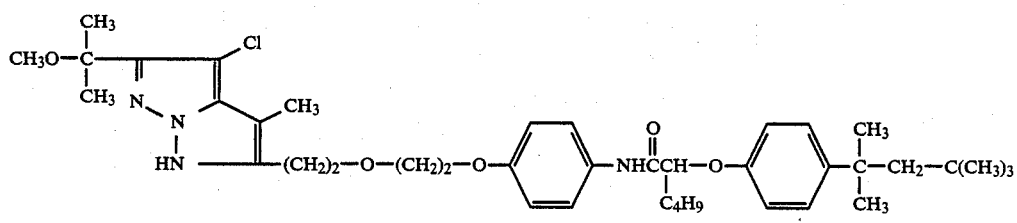 (M-7)
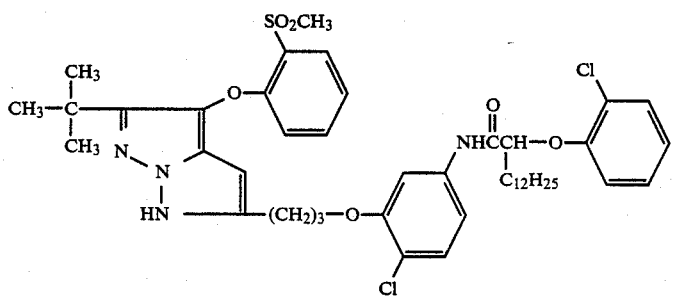 (M-8)
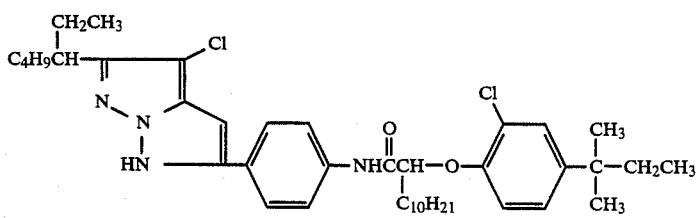 (M-9)
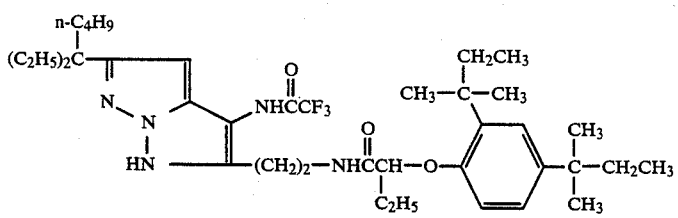 (M-10)
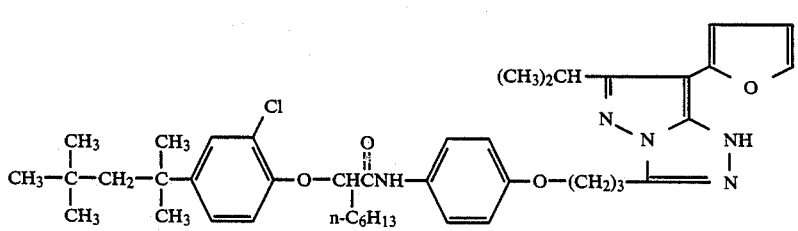 (M-11)
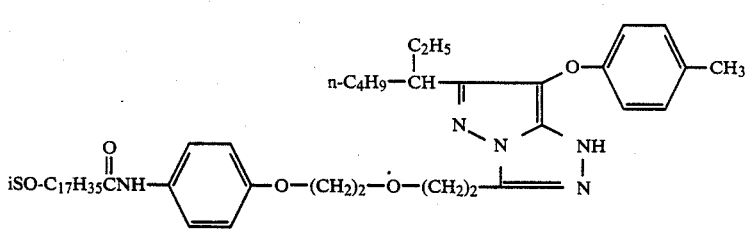 (M-12)

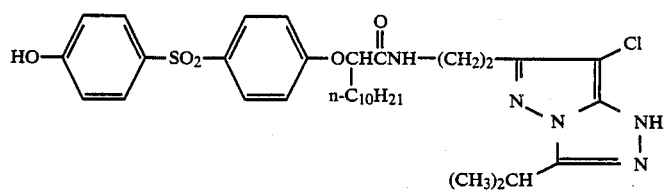
(M-13)
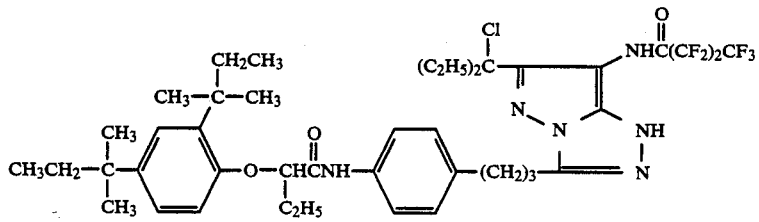
(M-14)
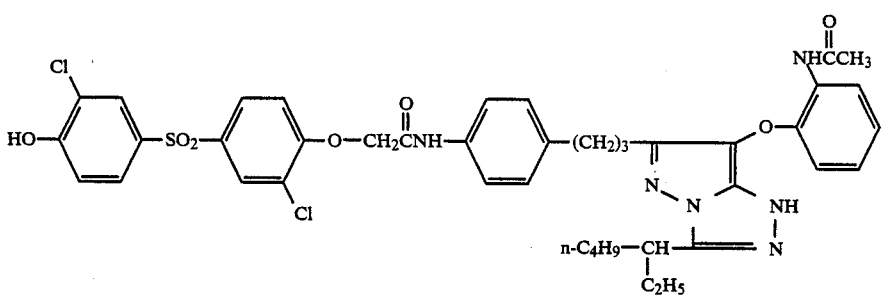
(M-15)
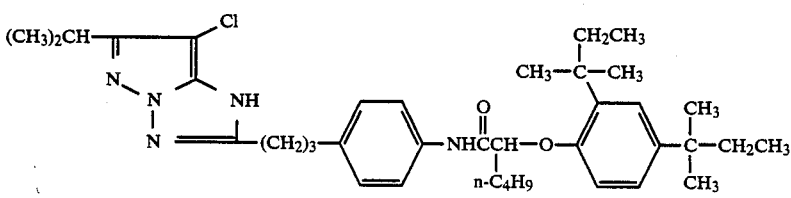
(M-16)
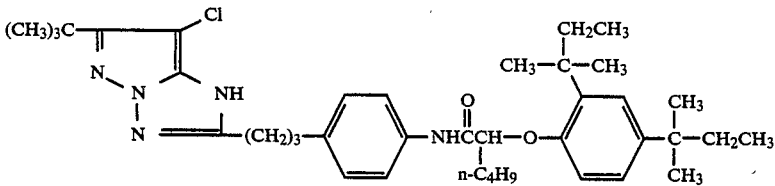
(M-17)
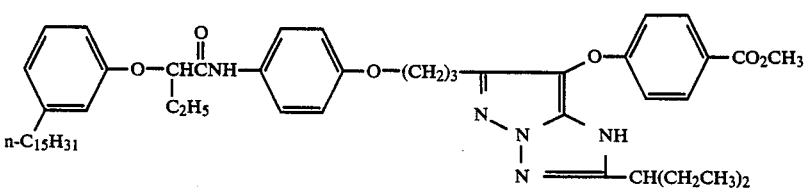
(M-18)
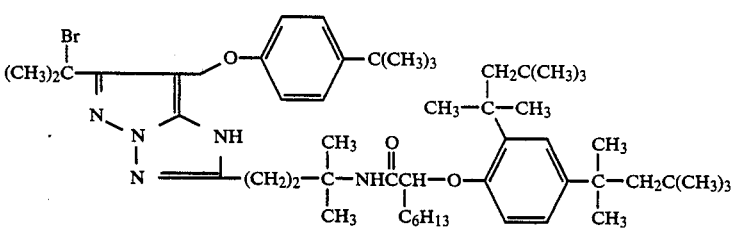
(M-19)

-continued
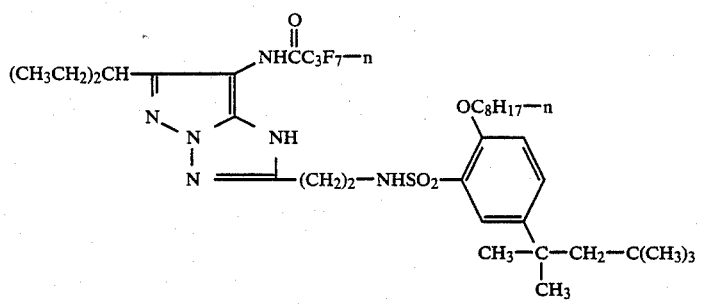
(M-20)
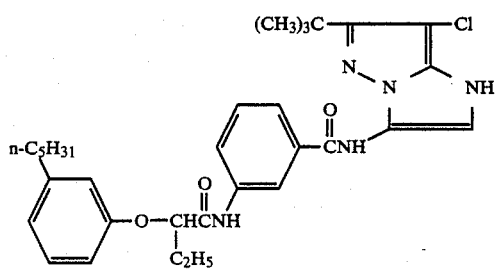
(M-21)
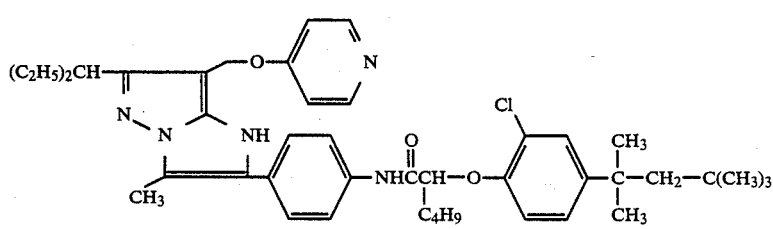
(M-22)
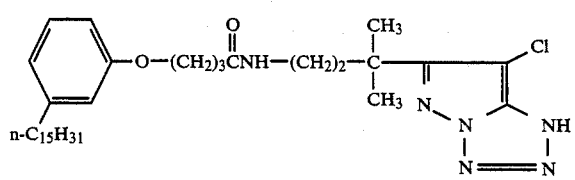
(M-23)
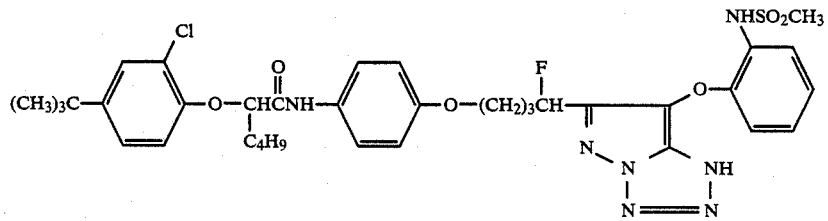
(M-24)
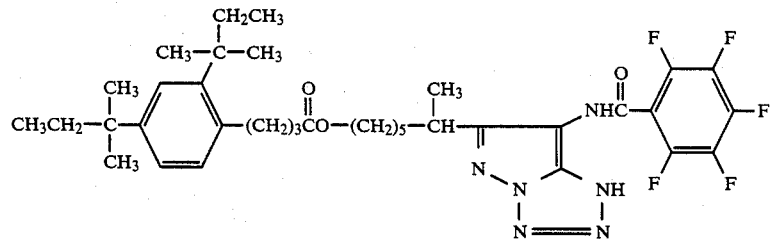
(M-25)

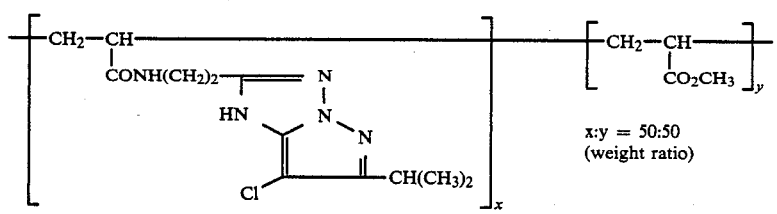
(M-26)
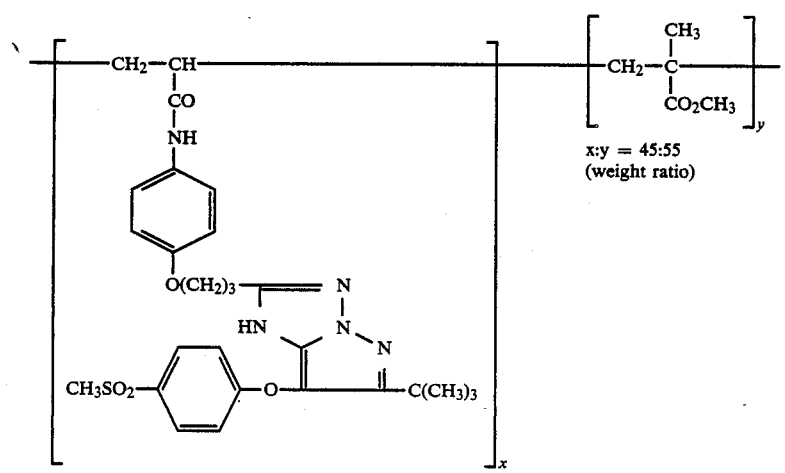
(M-27)
(M-28)
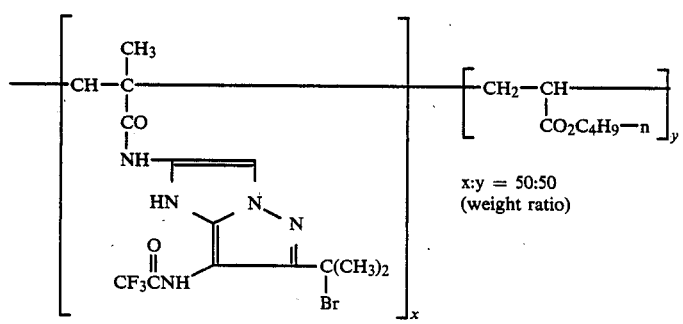
(M-29)
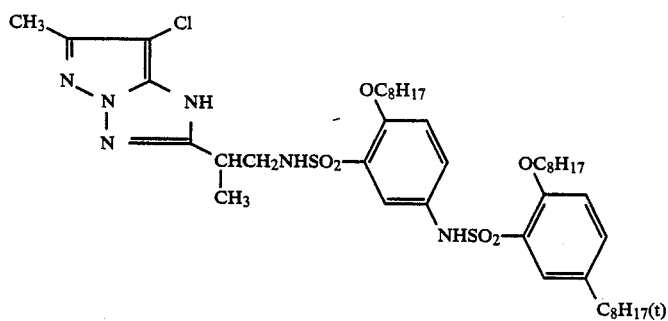
(M-30)
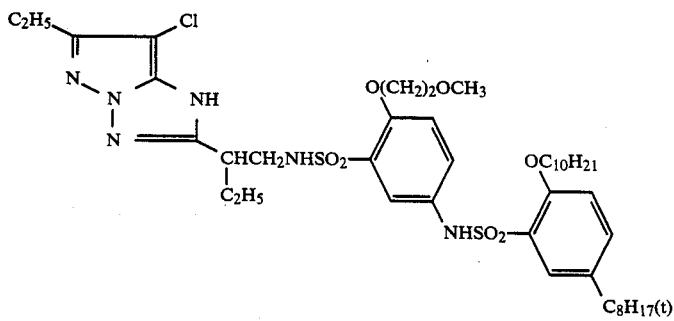

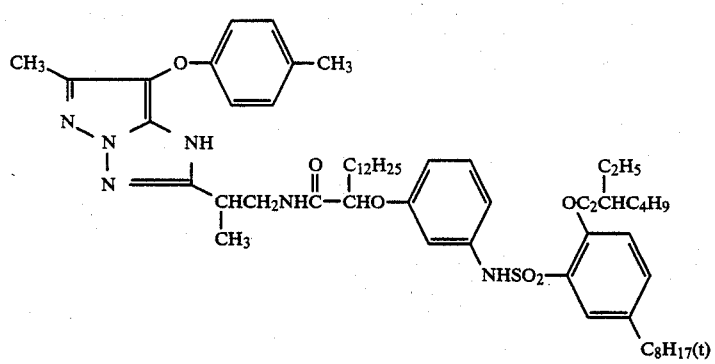 (M-31)
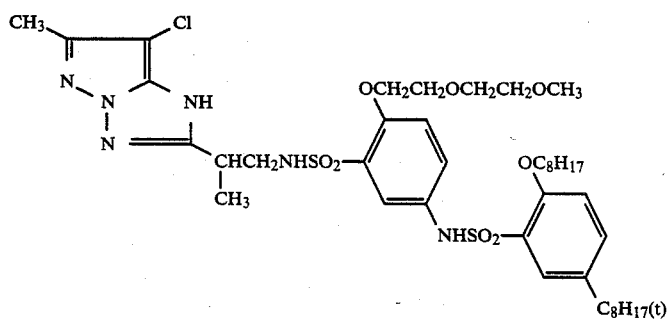 (M-32)
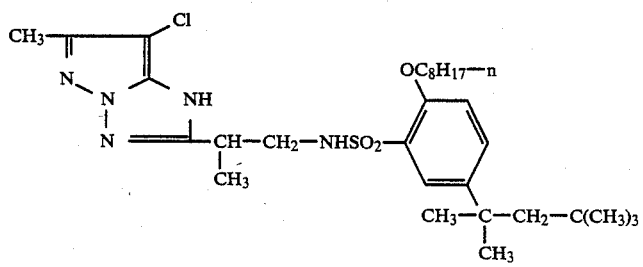 (M-33)
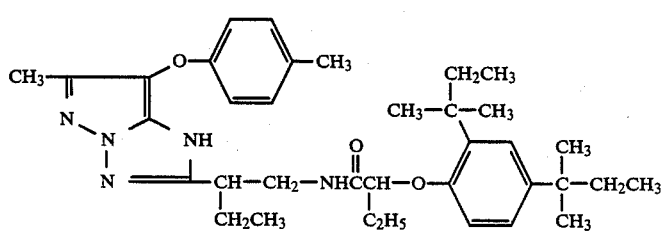 (M-34)
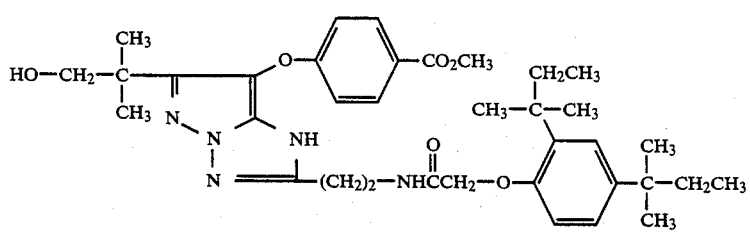 (M-35)

-continued

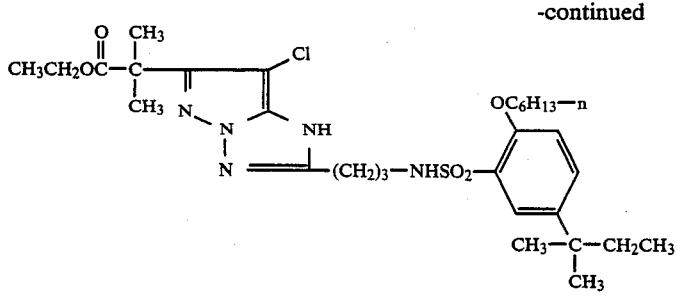
(M-36)

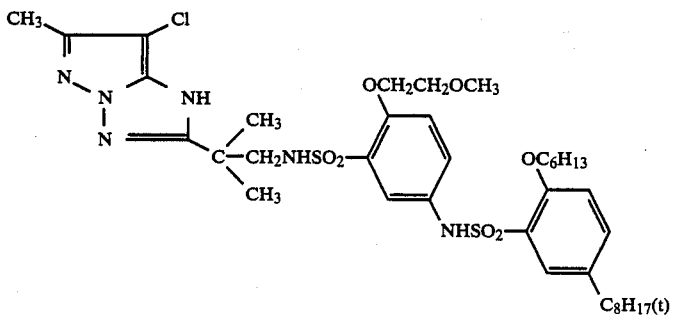
(M-37)

SYNTHESIS EXAMPLE

Synthesis of Coupler (M-16)

(1) Synthesis of 4-Methyl-3-oxopentanonitrile (A)

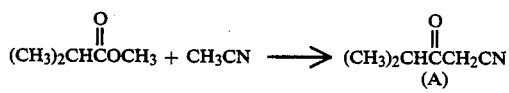

Tetrahydrofuran (800 ml) was stirred under a nitrogen stream at room temperature, and sodium hydride (60% dispersion in oil) was added thereto. The resulting suspension was heated over a steam bath and refluxed, and to the suspension was dropwise added a mixture of methyl 2-methylpropionate (102 g) and acetonitrile (45.2 g) over 2 hours and the reflux was continued for further 6 hours. After cooling the mixture, ethanol (50 ml) was added and the resulting mixture was stirred, followed by distilling off the solvent under reduced pressure. The residue was dissolved in water (1,000 ml) and washed twice with hexane (300 ml). Concentrated sulfuric acid (about 80 ml) was added to the aqueous layer to make it weak acidic, followed by extraction with ether (300 ml×3). The ether solution was dried over anhydrous magnesium sulfate and the ether portion was distilled off. The remaining pale yellow oily substance was distilled under reduced pressure (132.5°–134.5° C./48 mmHg) to obtain 47.9 g (43%) of 4-methyl-3-oxopentanonitrile (A).

Nuclear Magnetic Resonance Spectrum (CDCl$_3$): δ (ppm) 3.58 (2H, s), 2.80 (1H, m), 1.17 (6H, d, J=6.9 Hz).

(2) Synthesis of 5-Amino-3-(1-methylethyl)pyrazole (B)

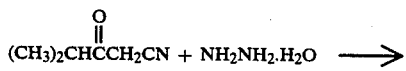

4-Methyl-3-oxopentanonitrile (A) was dissolved in ethanol (140 ml) and stirred at room temperature. Hydrazine hydrate (15.7 g) was added and the resulting mixture was stirred for 1 hour at room temperature, followed by heating under refluxing for 5 hours. The solvent was distilled off under reduced pressure and the residue was subjected to distillation under reduced pressure (133°–153° C./0.06 mmHg) to obtain 33.3 g (87%) of 5-amino-3-(1-methylethyl)pyrazole (B).

Nuclear Magnetic Resonance Spectrum (CDCl$_3$): δ (ppm) 6.03 (3H, br), 5.34 (1H, s), 2.83 (1H, m), 1.17 (6H, d, J=6.9 Hz).

(3) Synthesis of 6-(1-Methylethyl)-2-[3-(4-nitrophenyl)propyl]pyrazolo[1,5-b][1,2,4]triazole (C)

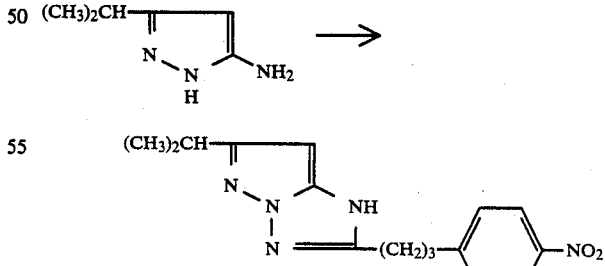

5-Amino-3-(1-methylethyl)pyrazole (12.5 g) was dissolved in methanol (40 ml) and to the resulting solution was added methyl 4-(p-nitrophenyl)butaneimidate hydrochloride (25.9 g) and the resulting mixture was stirred for 2 hours at room temperature. To this mixture was further added a methanol solution of hydroxylamine prepared by hydroxylamine hydrochloride (6.95 g) and a 28% methanol solution of sodium methoxide (19.3 g), and the resulting mixture was left to stand overnight at room temperature. After the solvent was distilled off under reduced pressure, the residue was added to water and extracted by ethyl acetate. The organic layer was dried over anhydrous magnesium sulfate and concentrated. The residue was dissolved in tetrahydrofuran (200 ml), and triethylamine (12.0 ml) was added and the resulting mixture was stirred in a water bath. p-Toluenesulfonic acid chloride (16.0 g) was gradually added to the mixture, and the resulting mixture was stirred for 1 hour without water bath. The insoluble matter was filtered off, and the filtrate was concentrated. The residue was dissolved in methanol (600 ml) and heated under refluxing for 3 hours. The methanol was distilled off under reduced pressure, and the residue was poured into water (1,000 ml) and extracted by ethyl acetate. The organic layer was dried over anhydrous magnesium sulfate, and concentrated. The residue was separated by the silica gel column chromatography (eluate: chloroform/ethyl acetate=5/1). The eluate containing the intended Compound (C) was concentrated, and the residue was recrystallized from ethyl acetate to obtain 6.2 g (20%) of 6-(1-methylethyl)-2-[3-(4-nitrophenyl)-propyl]-pyrazolo[1,5-b][1,2,4]triazole (C) as pale yellow crystals (m.p.: 188°–189° C.).

| Elemental Analysis | | | |
|---|---|---|---|
| | C | H | N |
| Calcd. (%): | 61.33 | 6.11 | 22.35 |
| Found (%): | 61.10 | 6.00 | 22.01 |

Nuclear Magnetic Resonance Spectrum (CDCl$_3$-DMSO-d$_6$): δ (ppm) 12.7 (1H, br), 8.12 (2H, d, J=9.0 Hz), 7.44 (2H, d, J=9.0 Hz), 5.45 (1H, s), 3.2–2.7 (5H, m), 2.15 (2H, m), 1.26 (6H, d, J=6.9 Hz).

(4) Synthesis of 2-[3-(4-Aminophenyl)propyl]-6-(1-methylethyl)pyrazolo[1,5-b][1,2,4]triazole (D)

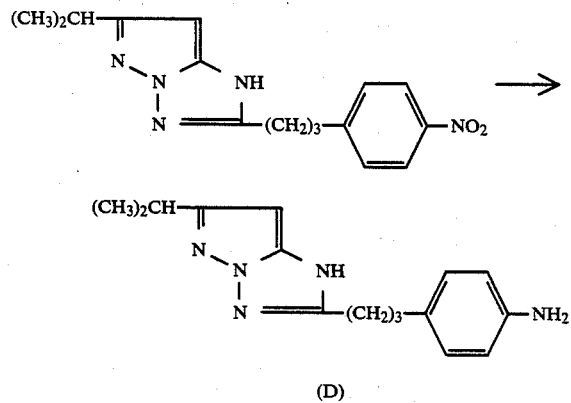

(D)

Reduced iron (6.7 g), ammonium chloride (0.53 g) and acetic acid (0.57 ml) were added to a mixed solvent of 2-propanol (40 ml) and water (8 ml), and the resulting mixture was heated over a steam bath and refluxed. To the mixture was further added the Nitro Compound (C) obtained in the step (3) above (6.27 g) and the reflux was further continued for 30 minutes. Sodium hydroxide (3.0 g) was dissolved in water (30 ml) and this solution was added to the above mixture. The resulting mixture was stirred and then filtered to remove insolubles. To the filtrate was added water (100 ml) and acetic acid (5 ml) and the resultant mixture was stirred. The resulting precipitated crystals were filtered and washed with water and dried to obtain 5.37 g (95%) of Amino Compound (D) as pale orange crystals (m.p.: 143.5°–144.5° C.).

(5) Synthesis of Compound (M-16)

Amino Compound (D) obtained in the step (4) above (5.04 g) was added to a mixed solvent of acetonitrile (30 ml) and N,N-dimethylacetamide (10 ml), and the resulting solution was stirred under heating over a steam bath. To this mixture was dropwise added 2-(2,4-di-t-amylphenoxy)hexanoyl chloride (6.86 g), and the resultant mixture was heated for further 10 minutes. The reaction mixture was poured into water (150 ml) and extracted by ethyl acetate. The organic layer was dried over anhydrous magnesium sulfate and then concentrated. The residue was dissolved in methylene chloride (200 ml), and N-chlorosuccinimide (2.16 g) was added thereto. The resultant mixture was stirred for 10 minutes at room temperature. This reaction mixture was washed 3 times with water (200 ml) and, then, dried over anhydrous magnesium sulfate. After concentration, the residue was separated by the silica gel column chromatography (eluate: chloroform/ethyl acetate=50/1), and the eluate was concentrated and dried and solidified to obtain 10.0 g (90%) of Coupler (M-16) as pale yellow powders.

| Elemental Analysis | | | |
|---|---|---|---|
| | C | H | N |
| Calcd. (%): | 70.40 | 8.39 | 10.80 |
| Found (%): | 70.15 | 8.37 | 10.57 |

Nuclear Magnetic Resonance Spectrum (CDCl$_3$): δ (ppm) 12.22 (1H, s), 7.99 (1H, s), 7.3–6.6 (7H, m), 4.73 (1H, t, J=4.8 Hz), 3.16 (1H, m), 2.8–2.6 (4H, m), 2.2–1.1 (30H, m), 1.0–0.5 (9H, m).

The magenta couplers of the present invention and other couplers which can be used in combination therewith (as described below) may be introduced into the photographic light-sensitive material by various known dispersion methods. Typical examples of such methods include the solid dispersion method, the alkali dispersion method, preferably the latex dispersion method, and more preferably the oil-in-water dispersion method. In the oil-in-water dispersion method, the couplers are dissolved in a high boiling organic solvent having a boiling point of 175° C. or more or in a so-called low boiling auxiliary solvent or in a mixture of these solvents, and then finely dispersed in an aqueous medium such as water or an aqueous gelatin solution in the presence of a surfactant. Examples of the high boiling organic solvents are described in U.S. Pat. No. 2,322,027 and will also be given below. The dispersion may involve a phase inversion, and the auxiliary solvent may be removed or reduced as required by distillation, noodle washing or ultrafiltration before coating on a support.

Examples of the high boiling organic solvents include phthalic esters (e.g., dibutyl phthalate, di-3,7-dimethyloctyl phthalate, dicyclohexyl phthalate, di-2-ethylhexyl phthalate, didodecyl phthalate, etc.), phosphoric or phosphonic esters (e.g., triphenyl phosphate, tricresyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate, di-2-ethylhexyl-phenyl phosphonate, etc.), benzoic esters (e.g., 2-ethylhexyl benzoate, dodecyl benzoate, 2-ethylhexyl-p-hydroxy benzoate, etc.), amides (e.g., diethyldodecaneamide, N-tetradecyl pyrrolidone, etc.), alcohols or phenols (e.g., isostearyl alcohol, 2,4-di-tert-amylphenol, etc.), aliphatic carboxylic esters (e.g., dioctyl azelate, glycerol tributylate, isostearyl lactate, trioctyl citrate, etc.), anilines (e.g., N,N-dibutyl-2-butoxy-5-tert-octylaniline, etc.), hydrocarbons (e.g., paraffin, dodecylbenzene, diisopropylnaphthalene, etc.). Suitable auxiliary solvents include organic solvents having a boiling point of about 30° C. to about 160° C. Typical examples thereof include ethyl acetate, butyl acetate, ethyl propionate, methyl ethyl ketone, cyclohexanone, 2-ethoxyethyl acetate; dimethylformamide, and the like. Of high boiling organic solvents, the above-mentioned phosphoric or phosphonic esters are most preferred.

The process of the latex dispersion method, its advantages and specific examples of the impregnating latexes are described in U.S. Pat. No. 4,199,363, West German patent application (OLS) Nos. 2,541,274 and 2,541,230 and the like.

The couplers of the present invention are preferably incorporated into the silver halide photographic emulsion layer. The amount of the coupler of the present invention is usually within the range of 0.003 to 0.5 mol per mol of silver halide and, the amount ranging from 0.005 to 0.3 mol per mol of silver halide can be preferably used for a color photographic light-sensitive material for taking picture, and the amount ranging from 0.1 to 0.3 mol per mol of silver halide is suitable for a color photographic light-sensitive material for print (color paper).

In the color photographic light-sensitive material of the present invention, conventional color couplers may be used in combination with the magenta couplers of the preset invention. Typical examples of the useful color couplers include naphthol or phenol compounds, pyrazolone or pyrazoloazole compounds and open chain or heterocyclic ketomethylene compounds. Specific examples of the cyan, magenta and yellow couplers which can be used in the present invention are described in patents cited in RD 17643 (Dec., 1978), item VII-D, and RD 18717 (Nov., 1979).

These couplers are preferably those having ballast groups or those which are polymerized so as to render the couplers nondiffusible. The coupling position is preferably substituted by a leaving group rather than a hydrogen atom. Couplers whose color-forming dyes have a suitable degree of diffusion, colored couplers, non-color-forming couplers or couplers capable of releasing a development restrainer or a development accelerator may also be employed in the present invention.

Yellow couplers which can be used in the present invention are typified by oil protected type acylacetamide couplers. Specific examples of these couplers are described in U.S. Pat. Nos. 2,407,210, 2,875,057 and 3,265,506 and the like. 2-Equivalent yellow couplers are preferably used in the present invention. Typical examples of these couplers include oxygen atom eliminating type yellow couplers as described in U.S. Pat. Nos. 3,408,194, 3,447,928, 3,933,501 and 4,401,752 and the like, or nitrogen atom eliminating type yellow couplers as described in Japanese Patent Publication No. 10739/83, U.S. Pat. Nos. 4,022,620 and 4,326,024, RD 18053 (Apr., 1979), British Pat. No. 1,425,020, West German patent application (OLS) Nos. 2,219,917, 2,261,361, 2,329,587 and 2,433,812 and the like. α-Pivaloyl acetanilide couplers are characterized in having color-forming dye stability, whereas -benzoyl acetanilide couplers are advantageous in having a good color-forming ability.

Conventional magenta couplers which can be used in the present invention include oil-protected type indazole or cyanoacetyl couplers, and preferably oil-protected 5-pyrazolone couplers. From the standpoint of hues of the color-forming dyes and the color-forming rates, the 5-pyrazolone couplers are preferably substituted at the 3-position thereof by an arylamino or acylamino group. Typical examples of these couplers are described in U.S. Pat. Nos. 2,311,082, 2,343,703, 2,600,788, 2,908,573, 3,062,653, 3,152,896 and 3,936,015 and the like. 2-Equivalent 5-pyrazolone couplers are preferred, and preferable leaving groups include a nitrogen eliminating group as described in U.S. Pat. No. 4,310,619 or an arylthio group as described in U.S. Pat. No. 4,351,897. The 5-pyrazolone couplers having a ballast group as described in European Pat. No. 73,636 have a superior color-forming ability.

Cyan couplers which can be used in the present invention include oil-protected type naphthal and phenol couplers. Typical examples thereof include naphthal couplers as described in U.S. Pat. No. 2,474,293, and oxygen atom elimination type highly activated 2-equivalent naphthal couplers as disclosed in U.S. Pat. Nos. 4,052,212, 4,146,396, 4,228,233 and 4,296,200 are preferred. Specific examples of phenol couplers are described in U.S. Pat. Nos. 2,369,929, 2,423,730, 2,772,162 and 2,895,826 and the like.

Cyan couplers which are stable against humidity and temperature are advantageously used in the present invention. Typical examples of these couplers include phenol cyan couplers as described in U.S. Pat. No. 3,772,002, 2,5-diacylamino substituted phenol couplers as described in U.S. Pat. Nos. 2,772,162, 3,758,308, 4,126,396, 4,334,011 and 4,327,173, West German patent application (OLS) No. 3,329,729 and U.S. Pat. No. 4,500,635 and the like, and phenol couplers having a phenylureido group at the 2-position and an acylamino group at the 5-position which are described in U.S. Pat. Nos. 3,446,622, 4,333,999, 4,451,559 and 4,427,767 and the like.

The couplers of the present invention and the above illustrated conventional couplers may be used in combination in one and the same layer in order to obtain the properties required for photographic light-sensitive materials. Needless to say, one and the same compound may be incorporated in two or more different layers.

In order to compensate for unnecessary absorption of the color-forming dyes of magenta and cyan couplers in a short wavelength region, it is preferable to use these couplers in combination with colored couplers in the color photographic light-sensitive materials for taking pictures. Typical examples of such colored couplers include yellow colored amgenta couplers as described in U.S. Pat. No. 4,163,670, Japanese Patent Publication No. 39413/82 and the like, or magenta colored cyan couplers as described in U.S. Pat. Nos. 4,004,929 and 4,138,258, British Pat. No. 1,146,368 and the like.

Colored couplers to be used in combination may also form dimers or polymers. Typical examples of polymer couplers are illustrated in U.S. Pat. Nos. 3,451,820 and 4,080,211. Specific examples of the polymer magenta couplers are described in British Pat. No. 2,102,173 and U.S. Pat. No. 4,367,282.

Graininess may be improved by using diffusible dye forming couplers in combination with the couplers of the present invention. Specific examples of such magenta couplers are described in U.S. Pat. No. 4,366,237 and British Pat. No. 2,125,570, and specific examples of such yellow, magenta and cyan couplers are illustrated in European Pat. No. 96,873 and West German patent application (OLS) No. 3,324,533.

As the binder or protective colloid which can be used in the emulsion layer or intermediate layer of the photographic light-sensitive material of the present invention, gelatin is advantageously employed, but other hydrophilic colloids may be used either singly or in combination with gelatin.

As the silver halide to be used in the photographic light-sensitive emulsion layer of the photographic light-sensitive material of the present invention, any one of silver bromide, silver iodobromide, silver iodochlorobromide, silver chlorobromide and silver chloride. Preferred silver halide is silver iodobromide containing not greater than 15 mol % of silver iodide. Particularly preferred is silver iodobromide containing 2 to 12 mol % of silver iodide.

The average size of the silver halide grains contained in the photographic light-sensitive emulsion (the grain size being defined as the grain diameter if the grain has a spherical or approximately spherical form and an edge length if the grain has a cubic form, and the average calculated based on the projected area) is not particularly limited, but is preferably below 3 μm.

The grain size distribution may be either narrow or broad.

The silver halide grains contained in the photographic light-sensitive emulsion may have a regular crystal form such as a cubic or octahedral form, or an irregular crystal form such as a spherical or tabular form, or a composite form of these crystal forms. The grains may be a mixture of these various crystal forms.

The silver halide grains may have a tabular form. In particular, emulsions containing 50% or more of tabular grains having a diameter/thickness ratio of 5 or more based on the projected area of the total grains may be employed.

A silver halide photographic emulsion which can be used in the present invention can be manufactured according to a method as disclosed in, for example, *RD* 17643 (Dec., 1978), pp. 22–23 "I. Emulsion preparation and types" and *RD* 18716 (Nov., 1979), p. 648.

Various photographic addenda which can be used in the present invention are disclosed in, for example, *Research Disclosure*, No. 17643, pages 23–28 and No. 18716, pages 648–651 (incorporated herein by reference) as illustrated below.

| Example of Addenda | RD No. 17643 Page | RD No. 18716 Page |
|---|---|---|
| (1) Chemical sensitizers | 23 | 648 right column |
| (2) Speed-increasing compound | | 648 right column |
| (3) Spectral sensitizers and supersensitizers | 23–24 | 648 right column to 649 right column |
| (4) Antifoggants and stabilizers | 24–25 | 649 right column |
| (5) Light-absorbing material, filter dyes, scattering materials | 25–26 | 649 right column to 650 right column |

| Example of Addenda | RD No. 17643 Page | RD No. 18716 Page |
|---|---|---|
| and ultraviolet absorbers | | |
| (6) Antistain agents | 25 right column | 650 left to right column |
| (7) Hardeners | 26 | 651 left column |
| (8) Vehicles and binding agents | 26 | 651 left column |
| (9) Plasticizers and lubricants | 27 | 650 right column |
| (10) Coating aids such as surfactants | 26–27 | 650 right column |
| (11) Agents for antistatic or conducting layers | 27 | 650 right column |

Suitable supports which can be used in the present invention are disclosed in, for example, idid., No. 17643, page 28 and No. 18716, page 647 right column to 648 left column (incorporated herein by reference).

A color photographic light-sensitive material according to the present invention can be processed by a conventional method as disclosed in, for example, ibid., 17643, pp. 28–29 and ibid., 18716, p. 651, left to right column.

The photographic light-sensitive material of the present invention may be washed with water after the color development processing or the bleach-fix processing. The color development processing can be effected at any temperature between 18° C. and 55° C. Color development processing is preferably conducted at a temperature higher than 30° C., and particularly preferably at a temperature higher than 35° C. The development time is within the range of about 1 minute to about 3.5 minutes, and is preferably short. For continuous development processing, the development solution is preferably replenished. The replenishment is effected at a ratio of 330 cc to 160 cc per square meter of the processed area, and preferably at a ratio of not greater than 100 cc. The amount of benzyl alcohol contained in the developer is preferably not more than 5 ml/1,000 ml. Bleach-fix processing may be carried out at any temperature ranging from 18° C. to 50° C., but temperatures higher than 30° C. are preferred. By raising the temperature higher than 35° C., the processing time may be reduced to 1 minute or less, and the amount of replenished solution may also be reduced. The time required for washing the photographic light-sensitive material with water after color development or bleach-fix is usually within 3 minutes and may be reduced to 1 minute or less by using a stabilizing bath.

Developed dyes undergo deterioration and discoloration by mildews during storage, aside from the deterioration due to light, heat or temperature. Cyan dye images particularly suffer from degeneration by mildews, and it is preferable to use an antifungus agent. Exemplary antifungus agents include 2-thiazolylbenzimidazoles as disclosed in Japanese patent application (OPI) No. 157244/82. Antifungus agents may be incorporated in the photographic light-sensitive materials or externally added during the development processing; they can be added by any suitable method provided that they are present in the photographic light-sensitive materials after the processing.

The present invention will now be described below with reference to the Examples, which should not be construed as limiting the scope of the present invention in any manner.

EXAMPLE 1

Tri(2-ethylhexyl)phosphate (18 ml) and ethyl acetate (25 ml) were added to Coupler (M-16) (8.9 g), and the resulting mixture was dissolved under heating. The obtained mixture was added to an aqueous solution (100 ml) containing gelatin (10 g) and sodium dodecylbenzenesulfonate (1.0 g), and the resultant mixture was stirred at a high speed to obtain a finely emulsified dispersion of the above-identified coupler. The total amount of this emulsified dispersion was added to a silver chlorobromide emulsion (100 g) (containing 6.5 g of Ag) comprising 50 mol % of Br, and 2% solution of a 2,4-dihydroxy-6-chloro-s-triazone sodium salt (10 ml) was added as the hardener. The obtained mixture was coated on a paper support laminated on both sides thereof with polyethylene to a silver coverage of 200 mg/m$^2$. A gelatin layer was further coated on the thus coated layer to obtain a sample. This sample was designated as Sample A.

Next, Sample B was prepared in a manner similar to that of preparing Sample A except that Coupler (M-16) was replaced by Coupler (M-17) (9.1 g).

Further, Sample C (comparative sample) was prepared in a manner similar to the above manner, using a compound of the following formula (8.9 g) as the comparative coupler.

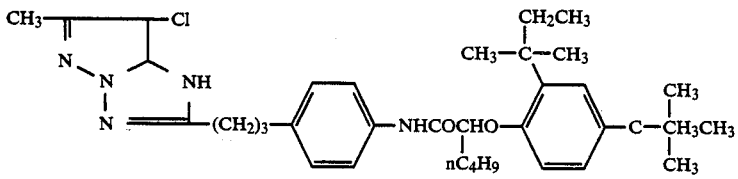

These three samples were subjected to wedge exposure (1,000 CMS) and processed with the following processing solutions to obtain magenta color images.

| Developing Solution: | |
|---|---|
| Benzyl Alcohol | 15 ml |
| Diethylenetriaminepentaacetic Acid | 5 g |
| KBr | 0.4 g |
| Na$_2$SO$_3$ | 5 g |
| Na$_2$CO$_3$ | 30 g |
| Hydroxylamine Sulfate Salt | 2 g |
| 4-Amino-3-methyl-N—β-(methane-sulfonamido)ethylaniline.3/2H$_2$SO$_4$.H$_2$O | 4.5 g |
| Water to make | 1,000 ml |
| | pH = 10.1 |
| Bleach-Fix Bath: | |
| Ammonium Thiosulfate (70 wt %) | 150 ml |
| Na$_2$SO$_3$ | 5 g |
| Na[Fe(EDTA)] | 40 g |
| EDTA | 4 g |
| Water to make | 1,000 ml |
| | pH = 6.8 |

| Processing Steps | Temperature (°C.) | Time |
|---|---|---|
| Developing Solution | 33 | 3 min 30 sec |
| Bleach-Fix Bath | 33 | 1 min 30 sec |
| Washing | 28–35 | 3 min |

The thus obtained magenta dye image of each sample was sharp and of high saturation. The photographic properties of these dye images were determined, and the results are shown in Table I.

TABLE I

| Sample | Sensitivity* | Gradation | Maximum Density |
|---|---|---|---|
| C (Comparative Sample) | 100 | 2.88 | 2.95 |
| A (Present Invention) | 100 | 2.96 | 2.97 |
| B (Present Invention) | 103 | 3.02 | 2.98 |

*A relative value of the reciprocal of the exposure amount giving a density of (fog + 0.5) with the value for the comparative sample being taken as 100.

As a result, it was found that the couplers of the present invention show approximately the same degree of sensitivity as the conventional couplers, but show superior gradation and maximum density.

EXAMPLE 2

Samples A, B and C prepared in Example 1 were processed in the same manner as Example 1 to obtain magenta dye images.

A portion of each of these samples was subjected to discoloration test at a high temperature of 100° C. for 7 days, and another portion was subjected to a discoloration test at a high temperature (60° C.) and high humidity (90%) environment for 6 weeks. Yet another portion was subjected to a xenon discoloration tester (100,000 lux) for 7 days with a UV filter which cuts UV light having a wavelength shorter than 390 nm placed in front of the sample. The magenta dye image stability was tested in this manner and the results obtained are shown in Table II.

TABLE II

| | Density Change of Magenta Dye Image | | |
|---|---|---|---|
| Sample | 100° C. 7 Days | 60° C., 90% RH 6 Weeks | Xenon (100,000) lux 7 Days |
| C (Comparative Sample) | 0.99 (0.14) | 0.98 (0.13) | 0.58 (0.13) |
| A (Present Invention) | 0.99 (0.13) | 0.99 (0.13) | 0.69 (0.13) |
| B (Present Invention) | 1.00 (0.12) | 1.00 (0.12) | 0.73 (0.13) |

The values show the magenta density after the discoloration test in areas having an initial density of 1.0.
The values in parentheses show the density values (stains) obtained by measuring the background with a blue filter.

From Table II, it can be seen that the couplers of the present invention have superior dye image stability even at a high temperature of 100° C. and under a high temperature (60° C.) and high humidity (90% RH) condition. The couplers of the present invention particularly excel in light fastness. Moreover, the remarkable fact is that no stain due to remaining couplers was found in any discoloration test.

EXAMPLE 3

Color photographic light-sensitive materials (Samples E, F and G) were prepared as shown in Table III by coating the first layer (lowermost layer) through the seventh layer (uppermost layer) one on top of another on a paper support laminated on both sides thereof with polyethylene.

The emulsified dispersion of the magenta coupler and a coating liquid composition containing the same used in the third layer were prepared in the same manner as in Example 1.

TABLE III

| | |
|---|---|
| First Layer (lowermost layer) | Blue sensitive silver chlorobromide emulsion (Br: 80 mol %, Ag: 350 mg/m²) Gelatin (1,500 mg/m²) Yellow coupler (*1) (500 mg/m²) Solvent (*2) (400 mg/m²) |
| Second Layer | Gelatin (1,100 mg/m²) Color mixing preventing agent (*3) (200 mg/m²) Solvent (*4) (100 mg/m²) |
| Third Layer | Green sensitive silver chlorobromide emulsion (Br: 50 mol %, Ag: 180 mg/m²) Magenta coupler (*5) (3.4 × 10⁻⁴ mol/m²) Solvent (*6) (Sample E: 410 mg/m², Sample F: 420 mg/m², Sample G: 410 mg/m²) |
| Fourth Layer | Gelatin (1,600 mg/m²) UV light absorber (*7) (700 mg/m²) Color mixing preventing agent (*3) (200 mg/m²) Solvent (*4) (300 mg/m²) |
| Fifth Layer | Red sensitive silver chlorobromide emulsion (Br: 50 mol %, Ag: 300 mg/m²) Gelatin (1,200 mg/m²) Cyan coupler (*8) (400 mg/m²) Solvent (*4) (250 mg/m²) |
| Sixth Layer | Gelatin (1,000 mg/m²) UV light absorber (*7) (360 mg/m²) Solvent (*4) (120 mg/m²) |
| Seventh Layer (uppermost layer) | Gelatin (1,600 mg/m²) |
| Support | A paper support laminated on both sides thereof with polyethylene |

Note: The amounts shown by mg/m² refer to coverage.
*1 Yellow coupler: α-Pivaloyl-α-(2,4-dioxo-5,5′-dimethyloxazolidin-3-yl)-2-chloro-5-[α-(2,4-di-tert-pentylphenoxy)-butanamido]acetanilide
*2 Solvent: Dioctylbutyl phosphate
*3 Color mixing preventing agent 2,5-Dioctylhydroquinone
*4 Solvent Dibutyl phthalate
*5 Magenta coupler Sample E: Coupler (M-16), Sample F: Coupler (M-17) and Sample G: Comparative Compound in Example 1
*6 Solvent Tri(2-ethylhexyl)phosphate
*7 UV light absorber 2-(2-Hydroxy-3-sec-butyl-5-tert-butylphenyl)-benzotriazole
*8 Cyan coupler 2-[α-(2,4-di-tert-pentylphenoxy)butanamido]-4,6-dichloro-5-methylphenol Separation filters (Blue, Green and Red) were applied to each of above Samples E, F and G, and the exposure and color development processing was carried out as in Example 1.

The obtained dye images were subjected to an exposure test using a fluorescent lamp fade tester (illuminance: 15,000 lux) for 4 weeks to check the magenta dye image stability. The results are shown in Table IV (the yellow stain values are shown in the parentheses).

TABLE IV

| | (dye image stability) |
|---|---|
| Sample | Fluorescent Lamp (15,000 lux) 4 Weeks |
| G (Comparative Sample) | 0.64 (0.13) |
| E (Coupler (M-16)) | 0.78 (0.13) |
| F (Coupler (M-17)) | 0.83 (0.12) |

From these results, it is shown that the dye images obtained by the couplers of the present invention have superior light fastness. It is also shown that the remaining couplers do not have any adverse effects on the light fastness of the dye images.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having coated thereon at least one silver halide emulsion layer, in which said silver halide emulsion layer or a layer adjacent thereto contains a magenta image-providing pyrazoloazole magenta coupler having substantially no dissolution in a developing solution and having at least one substituted alkyl group represented by the formula (I):

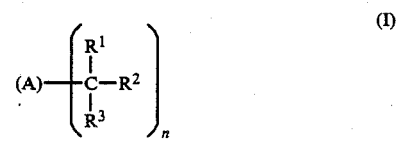

wherein (A) represents a pyrazoloazole magenta coupler residual group; $R^1$ is an alkyl group; $R^2$ and $R^3$ each is a hydrogen atom or a substituent, provided that both $R^2$ and $R^3$ are not hydrogen atoms at the same time; and n is 1 or 2, wherein said coupler is a coupler represented by the formula (VI):

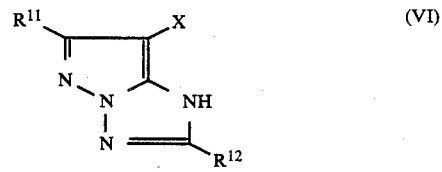

wherein at least one of $R^{11}$ and $R^{12}$ in formulae (VI) is an alkyl group of

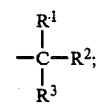

$R^1$ is a straight chain or branched chain or cyclic alkyl group; $R^2$ and $R^3$ each is a hydrogen atom or an alkyl group, provided that both $R^2$ and $R^3$ are not hydrogen atoms at the same time; when the substituents represented by $R^{11}$ and $R^{12}$ in formula (VI) are substituents other than the alkyl group of

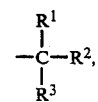

said substituents each is a hydrogen atom, a halogen atom, an alkyl group, an aryl group, a heterocyclic group, a cyano group, an alkoxy group, an aryloxy group, an acyloxy group, a carbamoyloxy group, a silyloxy group, a sulfonyloxy group, an acylamino group, an anilino group, a ureido group, an imido group, a sulfamoylamino group, a carbamoylamino group, an alkylthio group, an arylthio group, an alkoxycarbonylamino group, an aryloxycarbonylamino group, a sulfonamido group, a carbamoyl group, an acyl group, a sulfamoyl group, a sulfonyl group, sulfinyl group, an alkoxycarbonyl group, an aryloxycarbonyl group, a hydroxy group, an amino group or a carboxyl group; X is a hydrogen atom, a halogen atom, a carboxyl group, a group bonded via an oxygen atom or a group bonded via a sulfur atom; when $R^{11}$, $R^{12}$ or X is a divalent group, the coupler of the formula (VI) forms a di- or polymer; and when $R^{11}$, $R^{12}$ or X is a linking group, the coupler of the formula (VI) constitutes a partial structure of a vinyl monomer, in which said partial structure and the vinyl group are bonded via said linking group and wherein a

group is bonded directly to the pyrazoloazole nucleus at a position to which at least one of $R^{11}$ and $R^{12}$ is bonded.

2. A silver halide color photographic material as in claim 1, wherein the coupler is added in the silver halide emulsion layer.

3. A silver halide color photographic material as in claim 1, wherein the coupler is added in an amount of from 0.003 to 0.5 mol per mol of silver halide.

4. A silver halide color photographic material as in claim 1, wherein the photographic material is a color photographic light-sensitive material for taking picture and the amount of the coupler is from 0.005 to 0.3 mol per mol of silver halide.

5. A silver halide color photographic material as in claim 1, wherein the photographic material is a color photographic light-sensitive material for print and the amount of the coupler is from 0.1 to 0.3 mol per mol of silver halide.

6. A silver halide color photographic material as in claim 1, wherein said coupler is dissolved in droplets of a phosphoric or phosphonic ester as a high boiling organic solvent.

7. A silver halide color photographic material as in claim 6, wherein the phosphoric or phosphinic ester is triphenyl phosphate, tricresyl phosphate, 2-ethylhexyldiphenyl phosphate, tricyclohexyl phosphate, tri-2-ethyhexyl phosphate, tridodecyl phosphate, tributoxyethyl phosphate, trichloropropyl phosphate, or di-2-ethylhexylphenyl phosphonate.

8. A silver halide color photographic material as in claim 1, wherein the substituent represented by $R^{11}$ and $R^{12}$ in the formula (VI) which is a substituent other than the alkyl group of

is a heterocyclic oxy group.

9. A silver halide color photographic material as in claim 1, wherein the substituent represented by $R^{11}$ and $R^{12}$ in the formula (VI) which is substituent other than the alkyl group of

is a heterocyclic thio group.

* * * * *